(12) United States Patent
Nakano et al.

(10) Patent No.: US 9,816,095 B2
(45) Date of Patent: Nov. 14, 2017

(54) DOUBLE-STRANDED RIBONUCLEIC ACID FOR ADJUVANTS

(71) Applicant: KYOWA HAKKO BIO CO., LTD., Tokyo (JP)

(72) Inventors: Tetsuo Nakano, Tokyo (JP); Eitora Yamamura, Takaoka (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 14/650,229

(22) PCT Filed: Dec. 6, 2013

(86) PCT No.: PCT/JP2013/082774
§ 371 (c)(1),
(2) Date: Jun. 5, 2015

(87) PCT Pub. No.: WO2014/088087
PCT Pub. Date: Jun. 12, 2014

(65) Prior Publication Data
US 2015/0307884 A1    Oct. 29, 2015

(30) Foreign Application Priority Data

Dec. 6, 2012 (JP) ................................ 2012-267012
Jul. 11, 2013 (JP) ................................ 2013-145471

(51) Int. Cl.
| | | |
|---|---|---|
| *C12N 15/11* | (2006.01) | |
| *A61K 31/713* | (2006.01) | |
| *C12N 15/117* | (2010.01) | |
| *A61K 39/39* | (2006.01) | |

(52) U.S. Cl.
CPC .......... *C12N 15/117* (2013.01); *A61K 31/713* (2013.01); *A61K 39/39* (2013.01); *C12N 15/111* (2013.01); *C12N 2310/17* (2013.01); *C12N 2310/53* (2013.01); *C12N 2310/533* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 5,298,614 A | 3/1994 | Yano et al. | |
| 2004/0235044 A1 | 11/2004 | Matsuyama et al. | |

FOREIGN PATENT DOCUMENTS

| | | |
|---|---|---|
| EP | 1 029 544 A1 | 8/2000 |
| GB | 2207138 A | 1/1989 |
| JP | 01-104094 A | 4/1989 |
| JP | 01-238597 A | 9/1989 |
| WO | WO 99/20283 A1 | 4/1999 |
| WO | WO 00/47601 A1 | 4/2000 |
| WO | WO 2015/050191 A1 * | 4/2015 |
| WO | WO 2016/093358 A1 * | 6/2016 |
| WO | WO 2017/043490 A1 * | 3/2017 |

OTHER PUBLICATIONS

Powell et al, Clin. Exp. Immunol., 1972, 12:419-427.*
Heffernan et al, Biomaterials, 2009, 30:910-918.*
Matsumoto et al, Advanced Drug Delivery Reviews, 2008, 60:805-812.*
Matsumoto et al, Biochemical and Biophysical Research Communications, 2002, 293:1364-1369.*
Salem et al, Vaccine, 2006, 24:5119-5132.*
Meusel et al, Journal of Immunology, 2002, 168:6429-6435.*
Nicholson, Progress in Nucleic Acid Research and Molecular Biology, 1996, 52:1-65.*
Woodhour et al, "Hyperpotentiation by Synthetic Double-Stranded RNA of Antibody Responses to Influenza Virus Vaccine in Adjuvant 65 (33983)", Proceedings of the Society for Experimental Biology and Medicine. Society for Experimental Biology and Medicine (New York, N.Y.), 1969, 131:809-817.*
Desai et al., *Journal of Interferon and Cytokine Research*, 17(9): 531-536 (1997).
Haines et al., *Journal of Biological Chemistry*, 267(26): 18315-18319 (Sep. 15, 1992).
Kato et al., *Journal of Experimental Medicine*, 205(7): 1601-1610 (Jun. 30, 2008).
Machida et al., *Japanese Journal of Microbiology*, 20(2): 71-76 (1976).
Minks et al., *Journal of Biological Chemistry*, 255(13): 6403-6407 (Jul. 10, 1980).
Stewart II et al., *Journal of Genetic Virology*, 18: 237-246 (1973).
Stewart II et al., *Journal of Genetic Virology*, 23: 83-89 (1974).
Tytell et al., "Influence of Size of Individual Homopolynucleotides on the Physical and Biological Properties of Complexed $rI_n:rC_n$ (Poly I:C) (35170)," *Proceedings of the Society for Experimental Biology and Medicine*, 135(3): 917-921 (1970).
Japanese Patent Office, International Search Report in International Patent Application No. PCT/JP2013/082774 (dated Mar. 11, 2014).
Mills et al., *Nucleic Acids Research*, 32(13): 4055-4059 (2004).
European Patent Office, Supplementary European Search Report in European Patent Application No. 13861352 (dated Jul. 1, 2016).

* cited by examiner

*Primary Examiner* — Nita M Minnifield
(74) *Attorney, Agent, or Firm* — Leydig, Voit & Mayer, Ltd.

(57) ABSTRACT

The invention provides a double-stranded ribonucleic acid (dsRNA) having a chain length suitable for simultaneously showing low toxicity and high function in the use of an adjuvant and the like, and resisting variation of chain length even when subjected to a heating and cooling treatment, or a salt thereof; an immune potentiator, adjuvant, pharmaceutical product and the like containing the dsRNA and the like; and a production method of such dsRNA and the like. The invention is characterized in that the weight average chain length of two or more single-stranded ribonucleic acids (ssRNAs) constituting the first chain constituting dsRNA is not more than ½ of the weight average chain length of one ssRNA constituting the second chain.

2 Claims, No Drawings

DOUBLE-STRANDED RIBONUCLEIC ACID FOR ADJUVANTS

CROSS-REFERENCE TO RELATED APPLICATIONS

This patent application is the U.S. national phase of International Patent Application No. PCT/JP2013/082774, filed Dec. 6, 2013, which claims the benefit of Japanese Patent Application No. 2013-145471, filed on Jul. 11, 2013, and Japanese Patent Application No. 2012-267012, filed on Dec. 6, 2012, which are incorporated by reference in their entireties herein.

TECHNICAL FIELD

The present invention relates to a double-stranded ribonucleic acid highly useful as a pharmaceutical product or pharmaceutical additive and a production method thereof.

BACKGROUND ART

Living organisms have natural immune system that quickly recognizes and eliminates pathogens such as virus, bacterium and the like that entered the living body. In the living organisms invaded by pathogens, airway epithelial cells, dendritic cells and the like multilaterally recognize partial structure of pathogens via natural immunoreceptors such as Toll-like receptor, RIG-I-like receptor and the like, activate natural immunity and cause a natural immune response such as production of Type I interferon (IFN) and inflammatory cytokines. The constituent components of pathogens recognized by natural immunity and substances mimicing same are called Immune Potentiators, and applied researches thereof as an adjuvant for pharmaceutical products or vaccines are ongoing. Particularly, in the use for infection vaccines and cancer vaccines, its practicalization as an adjuvant capable of improving basic property while securing safety is expected. One of such immune potentiators is artificially synthesized double-stranded ribonucleic acid (dsRNA).

Representative examples of the artificially synthesized dsRNA include poly(A:U) wherein the single-stranded ribonucleic acids (ssRNAs) constituting a double-strand are adenylic acid homopolymer and uridylic acid homopolymer, poly(G:C) wherein ssRNAs constituting a double-strand are guanylic acid homopolymer and cytidylic acid homopolymer, polyIC wherein ssRNAs constituting a double-strand are inosinic acid homopolymer and cytidylic acid homopolymer, poly(I:C12U) wherein ssRNAs constituting a double-strand are polymer C12U of an about 12:1 mixture of cytidylic acid and uridylic acid and inosinic acid homopolymer, and the like. These homo dsRNAs, particularly polyIC and poly(I:C12U), are candidates for a therapeutic drug for viral diseases and anticancer drugs, and a number of basic researches and application studies have been conducted. Among them are reports on the observation of side reaction in non-clinical tests, and such finding is one of the matters of concern that prevent practicalization.

When the efficacy and side reaction of dsRNA such as polyIC and the like are discussed, the relationship with the chain length should be noted. A discussion with the knowledge of a finding that polyIC having a chain length of several kbp or more shows stronger toxicity than short chain polyIC is necessary.

The chain length as used in the present invention means the same as the base number of RNA. The unit of the chain length of ssRNA is expressed in base or kilobase (1 kb=1000 bases), and that of dsRNA is expressed in base pairs (bp) or kilobase pairs (1 kbp=1000 bp).

The weight average chain length of ssRNA and dsRNA is preferably a chain length determined by a gel permeation chromatography (GPC) analysis method. To be specific, GPC analysis is performed using dsRNA or dsDNA having a known molecular weight as a standard product, and average chain length and median value of the chain length are calculated from the obtained data. Another method includes determining sedimentation coefficient S (20,w) by a density gradient sedimentation velocity method, and estimating the chain length of ssRNA and dsRNA from an experimental formula (The Journal of Biochemistry (1961) 50:377).

Non-patent document 1 discusses the relationship between the chain length of polyIC and median lethal dose (LD50) in mouse intraperitoneal administration and describes that LD50 of polyIC decreases as the chain length becomes longer from 0.1 kbp to 6 kbp, namely, that the toxicity becomes stronger. To be specific, LD50 of polyIC having a centrifugation sedimentation coefficient 11.6 S (weight average chain length 2 kbp) is about ⅕ to that of polyIC having a centrifugation sedimentation coefficient 4.2 S (weight average chain length 0.1 kbp), and about ⅔ to that of polyIC having a centrifugation sedimentation coefficient 8.2 S (weight average chain length 0.8 kbp). Patent document 1 describes that a mouse intravenously administered with polyIC having a centrifugation sedimentation coefficient of not less than 13 S (i.e., weight average chain length of not less than 3 kbp) showed a 61% decrease in the bone marrow cell number, whereas a mouse intravenously administered with polyIC having a centrifugation sedimentation coefficient of 8 S (weight average chain length 0.75 kbp) did not show a decrease in the bone marrow cell number. Similarly, a mouse intravenously administered with poly(I:C12U) having a centrifugation sedimentation coefficient of not less than 13 S showed a 59% decrease in the bone marrow cell number, and a mouse intravenously administered with poly(I:C12U) having a centrifugation sedimentation coefficient of 9 S (weight average chain length 1.0 kbp) did not show a decrease in the bone marrow cell number.

On the other hand, non-patent document 1 describes that the strength of the Type I IFN inducing action of polyIC and the induction time are maintained more strongly and longer by polyIC having a longer chain length. Non-patent document 2 describes that chemically synthesized 70 bp polyIC shows RIG-1 binding ability in mouse fetal fibroblasts but the IFNβ induction activity markedly decreases as compared to 1.2 kbp polyIC. Non-patent document 3 describes that the chain length of dsRNA necessary for dsRNA dependent protein kinase reaction, which is one of the virus defense mechanisms that are activated by Type I IFN as a signal, and dsRNA dependent 2',5'-oligoA synthetase reaction is not less than about 40-60 bp.

With such findings as background, the chain length of dsRNA that functions as an adjuvant and has low toxicity is generally considered to be preferably 0.1 kbp-2.0 kbp.

Artificial homo dsRNA is generally obtained by a production method including synthesizing ssRNA by using ribonucleotide diphosphate as a substrate and enzymes such as poly ribonucleotide nucleotidyl transferase and the like, and forming a double-strand by an annealing treatment. The enzymatically synthesized ssRNA is, from the property of the enzymatic reaction, a mixture with various chain lengths. In addition, ssRNA is physicochemically unstable and, in our experience, a phosphodiester bond is broken in a neutral aqueous solution under an atmosphere of not less than about 50° C., thus resulting in the division of polymer. Furthermore, when homopolymers such as inosinic acid polymer and cytidylic acid polymer are annealed, plural ssRNAs are successively linked depending on the annealing conditions, as a result of which the average chain length of the resulting dsRNA becomes long. From such technical background, dsRNA reagents commercially available at present often have different average chain lengths according to the makers and according to lots, and the toxicity thereof is also assumed to be different for each product lot.

DOCUMENT LIST

Patent Document patent document 1: JP-A-1-238597

Non-Patent Documents non-patent document 1: Japanese Journal of Microbiology (1976) 20(2): 71-76
non-patent document 2: The Journal of Experimental Medicine (2008) 205 (7): 1601-1610
non-patent document 3: The Journal of Biological Chemistry (1980) 255(13): 6403-6407

SUMMARY OF THE INVENTION

Problems to be Solved by the Invention

To utilize dsRNA showing varying effectiveness and toxicity depending on the chain length for pharmaceutical products or clinical practice while securing safety, dsRNA resisting change of chain length is desired. During various studies of the production method of dsRNA, the present inventors encountered a phenomenon of formation of dsRNA having a chain length longer than expected when RNAs having almost the same average chain lengths were annealed. In one example, an inosinic acid homopolymer having an average chain length of about 400 bases and a cytidylic acid homopolymer having an average chain length of about 400 bases were annealed by heating and cooling, polyIC having not less than 2 kbp of redundant chain length components was produced. When polyIC was annealed under mild temperature decrease conditions after various studies, the chain length components of not less than 2 kbp decreased to some extent, but not less than 10 wt % remained even under the most successful conditions. When polyIC that showed decrease of not less than 2 kbp of the chain length components was heated and cooled again in a practical time frame hardly influencing other pharmaceutical components, not less than 2 kbp of chain length components increased again.

By checking the document data in the past, the average chain length of dsRNA produced by annealing ssRNAs having almost the same average chain lengths can be confirmed to be longer than the average chain lengths of ssRNAs constituting same. The above-mentioned non-patent document 1 describes information showing the average chain length of polyIC subjected to the experiment and the average chain lengths of inosinic acid homopolymer and cytidylic acid homopolymer used as materials thereof. In one example of data, polyIC produced by annealing an inosinic acid homopolymer with centrifugation sedimentation coefficient 6.9 S (weight average chain length 0.3 kb) and a cytidylic acid homopolymer with 6.5 S (weight average chain length 0.3 kb) is 16.0 S (weight average chain length 5.6 kbp). Thus, the phenomenon of long chain formation due to annealing artificial homoRNA having almost the same chain length occurs in any chain length area of from 2.2 S (weight average chain length 0.05 kb) to 12.0 S (weight average chain length 1.0 kb) of the chain length of RNA used.

As a means for short chain formation of dsRNA that underwent long chain formation, some methods including physicochemical cutting such as sonication, dry-heat treatment and the like are known. However, there is no study report on a production method suppressing long chain formation or a method of suppressing long chain formation from the structure of dsRNA, not to mention a known technique relating to the structure of dsRNA or means for preventing long chain formation thereof.

To use dsRNA for pharmaceutical products or use similar thereto, complete removal of pathogens such as mycoplasma, virus and the like having growth potential in the formulation process needs to be secured, for which heating sterilization is the most reliable treatment method. Therefore, a means for solving the serious problem in industrial utilization, that prevents practicalization of dsRNA-blended products, that it shows increased toxicity due to long chain formation by heating and cooling, is also desired.

An object of the present invention is to provide a dsRNA or a salt thereof which is safe as a pharmaceutical product or an adjuvant for vaccine, and a production method thereof, and further a safe dsRNA blended product.

Means of Solving the Problems

The present inventors have conducted intensive studies in an attempt to solve the aforementioned problems and found that long chain formation of the obtained dsRNA can be suppressed by setting the weight average chain length of ssRNA constituting one of the chains of dsRNA to not more than ½ to the weight average chain length of ssRNA constituting another chain. Furthermore, it was found that the thus-obtained dsRNA can suppresses an increase in the long chain components when a heating and cooling treatment is applied. The present inventors have further studied based on the above-mentioned findings and completed the present invention.

Accordingly, the present invention relates to the following [1]-[7].

[1] A double-stranded ribonucleic acid (dsRNA) having a weight average chain length within the range of 0.1 kilobase pairs (kbp) to 2.0 kbp, or a salt thereof, wherein the first chain of said dsRNA consists of two or more single-stranded ribonucleic acids (ssRNAs), and all of two or more ssRNAs constituting said first chain are homopolymers consisting of the same type of ribonucleotide,
the second chain of said dsRNA consists of one ssRNA, and each of two or more ssRNAs constituting said first chain has a base sequence having complementarity of a level capable of forming a double strand to a partial region of one ssRNA constituting said second chain, and
the weight average chain length of two or more ssRNAs constituting said first chain is not more than ½ to the weight average chain length of one ssRNA constituting said second chain.
[2] The dsRNA or a salt thereof of the above-mentioned [1], wherein said first chain is constituted of two or more ssRNAs having a weight average chain length of 0.02-1.0 kilobase (kb).

[3] The dsRNA or a salt thereof of the above-mentioned [1] or [2], wherein the weight ratio of dsRNA having a chain length of not less than 2 kbp is not more than 10% when an operation of heating said dsRNA or a salt thereof to 70° C. and cooling same to 35° C. at a drop rate of 2° C./h, and thereafter an operation of heating again to 70° C. and cooling same to 35° C. at an average drop rate of 5° C./min are performed.

[4] The dsRNA or a salt thereof of any one of the above-mentioned [1]-[3], wherein two or more ssRNAs constituting said first chain is polyinosinic acid and one ssRNA constituting said second chain is ssRNA comprising cytidylic acid at not less than 80%.

[5] An immune potentiator, an adjuvant, or a pharmaceutical product comprising the dsRNA or a salt thereof of any one of the above-mentioned [1]-[4].

[6] A method of producing double-stranded ribonucleic acid (dsRNA) having a weight average chain length within the range of 0.1 kilobase pairs (kbp) to 2.0 kbp, or a salt thereof, comprising (1) a step of preparing ssRNA consisting of the same type of ribonucleotide, (2) a step of preparing an ssRNA having a base sequence having complementarity of a level capable of forming a double strand to the aforementioned (1) ssRNA, and (3) a step of annealing the aforementioned (1) ssRNA and the aforementioned (2) ssRNA, wherein the weight average chain length of ssRNA in the aforementioned (1) is not more than ½ to that of the aforementioned (2) and is 0.02-1.0 kilobase (kb).

[7] The method of the above-mentioned [6], wherein ssRNA of the aforementioned (1) is a polyinosinic acid, and ssRNA of the aforementioned (2) is ssRNA containing cytidylic acid at a ratio of not less than 80%.

Effect of the Invention

Utilizing the findings disclosed in the present invention, a dsRNA resisting polymerization of dsRNAs, i.e., suppressing an increase in the toxicity caused by long chain formation, and a highly safe immune potentiator, adjuvant, vaccine and the like containing said dsRNA can be provided. The present invention also provides a production method of such dsRNA.

DESCRIPTION OF EMBODIMENTS (dsRNA or a Salt Thereof)

The present invention provides a novel dsRNA or a salt thereof (hereinafter these are sometimes to be referred to generically as "dsRNA of the present invention"). The dsRNA of the present invention characteristically has a weight average chain length within the range of 0.1 kilobase pairs (kbp) to 2.0 kbp, wherein the first chain of said dsRNA consists of two or more single-stranded ribonucleic acids (ssRNAs), and all of two or more ssRNAs constituting said first chain are homopolymers consisting of the same type of ribonucleotide, the second chain of said dsRNA consists of one ssRNA, and each of two or more ssRNAs constituting said first chain has a base sequence having complementarity of a level capable of forming a double strand to a partial region of one ssRNA constituting said second chain, and the weight average chain length of two or more ssRNAs constituting said first chain is not more than ½ to the weight average chain length of one ssRNA constituting said second chain.

As mentioned above, the first chain consists of two or more ssRNAs, and therefore, in the dsRNA of the present invention, two or more ssRNAs as the first chain may be bonded to ssRNA as the second chain via a complementary bond between ribonucleotides. In this event, all ssRNAs constituting the first chain constituting said dsRNA are not bonded via a phosphodiester bond, but include plural ssRNAs not directly bonded. In the present specification, irrespective of whether or not all ssRNAs are linked to form a "chain", of the two m chains constituting dsRNA, the side consisting of two or more ssRNAs is indicated as the first chain and the side consisting of one ssRNA is indicated as the second chain, for convenience.

All ssRNAs constituting the first chain are homopolymers consisting of the same type of ribonucleotide. The ssRNA may be, unlimitatively, for example, adenylic acid homopolymer, uridylic acid homopolymer, guanylic acid homopolymer, cytidylic acid homopolymer, inosinic acid homopolymer and the like.

ssRNA constituting the second chain has a base sequence complementary to ssRNA of said first chain at a level capable of forming, in the use environment of the dsRNA of the present invention, a double strand with each of two or more ssRNAs constituting the first chain. Accordingly, ssRNA as the second chain is not limited to a sequence wherein all bases are complementary to a base of ssRNA of the first chain. The use environment of dsRNA of the present invention presupposing administration to the living body refers to, for example, the condition of dissolving in saline at about 37° C. (pH about 7.4, sodium chloride concentration about 150 mM).

Therefore, for example, ssRNA as the second chain may be, obviously, ssRNA having a sequence combining one or plural kinds of ribonucleotides complementary to the ribonucleotide constituting each ssRNA of the first chain, as well as ssRNA further incorporating, as long as the complementary bond with ssRNA of the first chain is not markedly inhibited, ribonucleotide not complementary to the ribonucleotide constituting each ssRNA of the first chain at a frequency of less than 20%, preferably less than 10%, more preferably less than 5%, further more preferably less than 3%, particularly preferably less than 2%, most preferably less than 1%, in the all ribonucleotides constituting the ssRNA. The complementarity between bases of ribonucleotide is well known in the technical field.

To be specific, when the ssRNA of the first chain is an adenylic acid homopolymer, ssRNA as the second chain may be, obviously, ssRNA of a sequence combining one or plural kinds of ribonucleotides selected from uridylic acid and inosinic acid, as well as ssRNA further incorporating, as long as the complementary bond with ssRNA of the first chain is not markedly inhibited, adenylic acid and/or guanylic acid and/or cytidylic acid and/or xanthylic acid at a frequency of less than 20%, preferably less than 10%, more preferably less than 5%, further more preferably less than 3%, particularly preferably less than 2%, most preferably less than 1%, in the all ribonucleotides constituting the ssRNA.

When the ssRNA of the first chain is a uridylic acid homopolymer, ssRNA as the second chain may be, obviously, ssRNA of a sequence of adenylic acid, as well as ssRNA further incorporating, as long as the complementary bond with ssRNA of the first chain is not markedly inhibited, uridylic acid and/or guanylic acid and/or inosinic acid and/or cytidylic acid and/or xanthylic acid at a frequency of less than 20%, preferably less than 10%, more preferably less than 5%, further more preferably less than 3%, particularly preferably less than 2%, most preferably less than 1%, in the all ribonucleotides constituting the ssRNA.

When the ssRNA of the first chain is a guanylic acid homopolymer, ssRNA as the second chain may be, obviously, cytidylic acid homopolymer, as well as ssRNA further incorporating, as long as the complementary bond with ssRNA of the first chain is not markedly inhibited, uridylic acid and/or adenylic acid and/or guanylic acid and/or inosinic acid and/or xanthylic acid at a frequency of less than 20%, preferably less than 10%, more preferably less than 5%, further more preferably less than 3%, particularly preferably less than 2%, most preferably less than 1%, in the all ribonucleotides constituting the ssRNA.

When the ssRNA of the first chain is a cytidylic acid homopolymer, ssRNA as the second chain may be, obviously, ssRNA of a sequence combining one or plural kinds of ribonucleotides selected from guanylic acid and inosinic acid, as well as ssRNA further incorporating, as long as the complementary bond with ssRNA of the first chain is not markedly inhibited, adenylic acid and/or uridylic acid and/or cytidylic acid and/or xanthylic acid at a frequency of less than 20%, preferably less than 10%, more preferably less than 5%, further more preferably less than 3%, particularly preferably less than 2%, most preferably less than 1%, in the all ribonucleotides constituting the ssRNA.

When the ssRNA of the first chain is an inosinic acid homopolymer, ssRNA as the second chain may be, obviously, ssRNA of a sequence combining one or plural kinds of ribonucleotides selected from adenylic acid and cytidylic acid, as well as ssRNA further incorporating, as long as the complementary bond with ssRNA of the first chain is not markedly inhibited, uridylic acid and/or guanylic acid and/or inosinic acid and/or xanthylic acid at a frequency of less than 20%, preferably less than 10%, more preferably less than 5%, further more preferably less than 3%, particularly preferably less than 2%, most preferably less than 1%, in the all ribonucleotides constituting the ssRNA. In one embodiment, ssRNA of the first chain is an inosinic acid homopolymer, ssRNA as the second chain is an ssRNA containing cytidylic acid at a ratio of not less than 80%, ssRNA of the first chain is, for example, an inosinic acid homopolymer, and ssRNA as the second chain is a cytidylic acid homopolymer, and the like.

Whether the produced RNA has formed a double strand can be determined by, for example, examining the temperature-absorbance curve utilizing the difference between ssRNA and dsRNA in the absorption coefficient at Abs 260 nm. That is, the feature that the absorption at Abs 260 nm derived from nucleic acid base decreases by hydrogen bond of nucleic acid bases is utilized. To be specific, RNA sample is diluted with saline, filled in a quartz cell, the absorbance is continuously measured while gradually heating the quartz cell by a spectrophotometer equipped with a temperature control function, and a temperature-absorbance curve is measured. When the sample is dsRNA, Abs 260 nm sharply increases from the temperature at which hydrogen bond between ssRNAs is broken and dissociation into ssRNA begins, and therefore, its temperature-absorbance curve becomes a sigmoid curve. When the sample is an ssRNA mixture free of double strand formation, its temperature-absorbance curve becomes linear.

The dsRNA of the present invention has a weight average chain length within the range of 0.1 kbp to 2.0 kbp, more preferably 0.1 kbp to 1.0 kbp, further more preferably 0.2 kbp to 0.6 kbp.

In the dsRNA of the present invention, the weight average chain length of two or more ssRNAs constituting the first chain is not more than ½ to that of one ssRNA constituting the second chain. Specifically, the weight average chain length of ssRNA constituting the first chain is, for example, 0.02-1.0 kb, preferably 0.02-0.4 kb, more preferably 0.02-0.2 kb. On the other hand, the weight average chain length of ssRNA of the second chain is, for example, 0.04-2.0 kb, preferably 0.04-0.8 kb, more preferably 0.04-0.4 kb. By setting the weight average chain length of ssRNA constituting the first chain to, for example, 0.02-0.1 kb, preferably 0.02-0.05 kb, and that of the second chain to, for example, 0.2-1.0 kb, preferably 0.3-0.6 kb, dsRNA recognized by RLR but not easily recognized by TLR-3 can be obtained.

As described above, the weight average chain length can be determined by a GPC analysis method. While the chain length may be calculated by an agarose gel electrophoresis method or polyacrylamide gel electrophoresis, since electrophoresis buffer has a low salt concentration, dsRNA may be problematically dissociated and cleaved partially during electrophoresis and chain length distribution cannot be analyzed with high precision. Therefore, chain length with low accuracy which is estimated by an agarose gel electrophoresis method or polyacrylamide gel electrophoresis cannot be compared with the data shown in the Examples of the present invention.

GPC analysis can be performed using a GPC analysis system mounting a water-soluble GPC analysis column. In this case, it is important to perform analysis while maintaining a high salt concentration of an eluent and low column temperature. Specifically, for example, GPC analysis can be performed as follows. As a GPC analysis system, LC Solution GPC manufactured by Shimadzu Corporation is used, chromatography is performed in an isocratic mode, and absorbance intensity at Abs 260 nm is measured. As the column, TSKgel G5000PWXL (manufactured by Tosoh Corporation) is used for the analysis of dsRNA of 4000 bp or below. As a molecular weight marker, mononucleotide and oligonucleotide produced by an automatic synthesizer, and various DNA fragments of about 100 bp to about 4000 bp obtained by amplification of suitable DNA sequence by PCR method using λDNA as a template are used.

Analysis conditions are as described below.
  eluent: 10 mM tris sulfuric acid buffer (pH 7.0), 150 mM sodium sulfate
  pump flow rate: 0.5 ml/min
  column: TSK-Gel G-5000PWXL
  column temperature: 25° C.
  UV detection: Abs 260 nm The absorbance intensity at Abs 260 nm output from LC-Solution GPC needs to be retreated by spreadsheet software and the like. This is because the recorded absorbance data at Abs 260 nm show a product of RNA concentration and chain length number of RNA, rather than the concentration of RNA. Matrix of time-course absorbance data and GPC molecular weight data recorded on LC-Solution GPC is loaded onto spreadsheet software, the base number is determined from the GPC molecular weight, the absorbance is divided by the base number to give value A, value A and molecular weight data are statistically processed and weight average chain length and median value (chain length at which value A becomes the local maximum) are determined. As the relational formula of the base number of RNA synthesized by poly ribonucleotide nucleotidyl transferase and GPC molecular weight, the following calculation formula can be used.

for ssRNA base number=(GPC molecular weight-98)/(NMP-18)

NMP: average molecular weight of nucleotide monophosphate for dsRNA base number=(GPC molecular weight-196)/(NMP1+NMP2-36)

NMP1: average molecular weight of sense side nucleotide monophosphate

NMP2: average molecular weight of antisense side nucleotide monophosphate

The structure of the 5'-terminal and 3'-terminal of dsRNA in the present invention may be any. Specifically, the 5'-terminal may be any of hydroxyl, monophosphate, diphosphate and triphosphate, and the 3'-terminal may be any of hydroxyl, monophosphate, diphosphate and triphosphate.

Examples of the salt of dsRNA of the present invention include metal salt, ammonium salt, organic amine addition salt, amino acid addition salt and the like. Examples of the metal salt include alkali metal salts such as sodium salt, potassium salt and the like, alkaline earth metal salts such as magnesium salt, calcium salt and the like, aluminum salt, zinc salt and the like. Examples of the ammonium salt include salts such as ammonium, tetramethylammonium and the like. Examples of the organic amine addition salt include salts such as trishydroxyaminomethane and the like. Examples of the amino acid addition salt include salts such as lysine, arginine, histidine, tryptophan, ornithine and the like.

(Immune Potentiator, Adjuvant, Pharmaceutical Product)

The dsRNA of the present invention may be added singly to vaccine and pharmaceutical products, or can be combined with other components or used in combination with drug forming techniques. For example, utilization as a hybrid polymer hydrogen bonded with a cationic polymer such as polylysine, polyglutamic acid and the like, mixing with other immune potentiator having a different signal transduction pathway, utilization as a liposome preparation contained in or adsorbed to various liposome substrates such as oil-in-water type emulsion and the like, utilization as a preparation for improving spreading capability by mixing with a thickener can be mentioned. Furthermore, it can also be combined with a drug delivery technique and a skin patch preparation technique. Furthermore, it can also be used by mixing with an immune potentiator having a different signal transduction pathway.

The object of use of the dsRNA of the present invention, and a mixture thereof is not only improvement of the property of pharmaceutical products having other active ingredients, such as vaccine, anticancer drug, protein medicament, antibody medicament, nucleic acid medicament and the like, but also utilization of dsRNA of the present invention as an active ingredient of pharmaceutical product, animal drug, fishery drug. The dosage form may be any such as injection, nasal drop, eye drop, percutaneous absorber and the like.

(Production Method)

The present invention also provides a production method of dsRNA or a salt thereof (hereinafter the production method of the present invention). The method includes (1) a step of preparing ssRNA consisting of the same type of ribonucleotide, (2) a step of preparing an ssRNA having a base sequence having complementarity of a level capable of forming a double strand to the aforementioned (1) ssRNA, and (3) a step of annealing the aforementioned (1) ssRNA and the aforementioned (2) ssRNA, wherein the weight average chain length of ssRNA in the aforementioned (1) is not more than ½ to that of the aforementioned (2) and is 0.02-1.0 kilobase (kb).

ssRNA in steps (1), (2) can be similar to those described above as ssRNA constituting the first chain and the second chain of dsRNA of the present invention, using which the dsRNA of the present invention can be produced.

In steps (1), (2), ssRNA can be chemically synthesized using a commercially available RNA synthesizer and ribonucleotide monophosphate as a starting material. Also, it can be enzymatically synthesized from ribonucleotide triphosphate by using a commercially available RNA polymerase and deoxyribonucleic acid as a template. In addition, it can also be synthesized enzymatically from ribonucleotide diphosphate by using a commercially available poly ribonucleotide nucleotidyl transferase, without using a template. For preparation of ssRNA, for example, a method described in a document [JP-A-2-227077] and the like may also be utilized as appropriate.

While ssRNA enzymatically synthesized by poly ribonucleotide nucleotidyl transferase often has an average chain length exceeding 2 kb, ssRNA with a shorter chain length can be obtained by extending the reaction time. For short chain formation of RNA, any method can be used such as sonication, dry-heat treatment of solid, alkali treatment, enzymatic treatment using an RNA degrading enzyme and the like.

Purification of synthesized ssRNA and purification of dsRNA obtained by annealing same can be performed by a known method such as dialysis, precipitate filtration, column purification and the like. Purified ssRNA and dsRNA can be acquired as an 1-20 mg/ml aqueous solution, or can be acquired as a solid by a further treatment such as freeze-drying and the like.

The annealing operation in step (3) can be performed by a known method described in non-patent document 1 and the like. As ssRNA to be used for annealing, both purified ssRNA and unpurified ssRNA may be used.

When a salt of dsRNA is to be acquired, dsRNA obtained in the form of a salt may be directly purified, or dsRNA obtained in a free form may be dissolved in water, cation is added to form a salt, which may be purified by a conventional method such as precipitate filtration, column purification and the like.

Experimental Examples and Comparative Examples are shown below.

EXPERIMENTAL EXAMPLE 1

GPC Analysis

Inosinic acid homopolymer and cytidylic acid homopolymer enzymatically synthesized by poly ribonucleotide nucleotidyl transferase were diluted with sample diluent [10 mM tris sulfuric acid buffer (pH 7.0), 150 mM sodium sulfate], and subjected to GPC analysis. As the GPC analysis system, LC Solution GPC manufactured by Shimadzu Corporation mounting TSKgel G5000PWXL packed column (manufactured by Tosoh Corporation) was used, chromatography was performed in an isocratic mode, and absorbance intensity at Abs 260 nm was measured. As a molecular weight marker, mononucleotide and oligonucleotide produced by an automatic synthesizer, and DNA fragments of about 4000 bp to about 100 bp obtained by amplification by PCR method using XDNA as a template were used.

The analysis conditions are as follows.
eluent: 10 mM tris sulfuric acid buffer (pH 7.0), 150 mM sodium sulfate
pump flow rate: 0.5 ml/min
column: TSK-Gel G-5000PWXL
column temperature: 25° C.
detection: Abs 260 nm Matrix of the time-course absorbance data and GPC molecular weight data recorded on LC-Solution GPC was loaded onto spreadsheet software. Then, on the spreadsheet software, the base number (chain length) was calculated from GPC molecular weight, the absorbance was divided by base number (chain length) to give value A, the corresponding data of the base number (chain length) and value A were statistically processed, and the weight average chain length and median value were calculated. Furthermore, wt % of the chain length component of not less than 2 kb was calculated.

The calculation formulas used for calculation of the base numbers (chain length) of the inosinic acid homopolymer and cytidylic acid homopolymer are as follows.

inosinic acid homopolymer: base number (chain length)=(GPC molecular weight-98)/330.2 cytidylic acid homopolymer: base number (chain length)=(GPC molecular weight-98)/305.2

The analysis results are shown in Table 1.

TABLE 1

| sample name | substance | weight average chain length (base) | median value (base) | >2 kb ratio (wt %) |
|---|---|---|---|---|
| pI-400 | inosinic acid homopolymer | 389 | 381 | 0.9 |
| pC-400 | cytidylic acid homopolymer | 344 | 324 | 0.8 |

COMPARATIVE EXAMPLE 1

Production of dsRNA

Inosinic acid homopolymer pI-400 was dissolved in annealing buffer [composition: 100 mM HEPES buffer (pH 6.5), 100 mM NaCl] to produce a solution (10 ml) such that Abs 260 nm of 50-fold diluent was 1.0. Similarly, cytidylic acid homopolymer pC-400 was dissolved in annealing buffer to produce a solution (10 ml) such that Abs 260 nm of 50-fold diluent was 1.0. To a 50 ml plastic tube were added pI-400 solution (5 ml) and pC-400 solution (5 ml), and two tubes containing the mixture was produced and stood at room temperature for 16 hr. 4M NaCl solution (0.5 ml) and isopropyl alcohol (10 ml) were added and mixed in each tube, polyIC was precipitated by centrifugation at 2800×g for 10 min, and the centrifugation supernatant was removed. 70% Ethanol (20 ml/tube) was added and mixed, polyIC was re-precipitated by centrifugation at 2800×g for 10 min, and the centrifugation supernatant was removed. 70% Ethanol (20 ml/tube) was added again and mixed, polyIC was re-precipitated by centrifugation at 2800×g for 10 min, and the centrifugation supernatant was removed. The tube was placed in a desiccator, and remaining ethanol was evaporated by drying under reduced pressure. Thereafter, annealing buffer was added at 10 ml/tube to give polyIC (400:400) solutions #1 and #2 (#1 and #2 shows they were obtained by independent operation).

COMPARATIVE EXAMPLE 2

GPC Analysis of dsRNA

The chain lengths of polyIC (400:400) #1 and #2 obtained in Comparative Example 1 were analyzed by GPC analysis.

The GPC analysis was performed using the apparatus and procedures described in Experimental Example 1, and the correspondence data of polyIC base pairs number (chain length) and value A were statistically processed to calculate mean weight and median value. Furthermore, wt % of not less than 2000 base pairs (2 kbp) was calculated.

The polyIC chain length was calculated by the following calculation formula.

polyIC: chain length (bp)=(GPC molecular weight-196)/635.4

The calculation results are shown in Table 2.

It was clarified that polyIC produced by polymerizing inosinic acid homopolymer having a weight average chain length of 389 bases which is shorter than 2 kb and cytidylic acid homopolymer having a weight average chain length of 344 bases contains 42-43% (weight ratio) of chain component of not less than 2 kbp which is considered to be problematic. The chain component of not less than 2 kbp is assumed to have been formed by plural cytidylic acid homopolymer and inosinic acid homopolymer used as materials, which are connected to each other.

TABLE 2

| | #1 | | | #2 | | |
|---|---|---|---|---|---|---|
| | chain length (bp) | | >2 kbp | chain length (bp) | | >2 kbp |
| sample name | weight mean | median value | ratio (wt %) | weight mean | median value | ratio (wt %) |
| polyIC (400:400) | 993 | 792 | 42 | 1017 | 792 | 43 |

COMPARATIVE EXAMPLE 3

Consideration of Heating and Cooling Conditions

The heating and cooling treatments were performed by the following procedures.

PolyIC (400:400) #1 and #2 produced in Comparative Example 1 were each dispensed by 1 ml to a plastic tube (inner volume 1.5 ml) with a screw cap, and a heating and cooling treatment was performed under the following conditions 1, 2 or 3.

Condition 1: After incubation in a warm bath (75° C.) for 3 min to raise the product temperature to 70° C., the product was left standing at room temperature (about 26° C.). The time required for cooling to 35° C. was about 7 min, and an average temperature decrease rate was 5° C./rain.

Condition 2: After incubation in a warm bath (75° C.) for 3 min to raise the product temperature to 70° C., the heater power of the warm bath was switched off, and the product was allowed to gradually cool to 35° C. The time required for cooling to 35° C. was about 2 hr.

Condition 3: After incubation in a warm bath (75° C.) for 3 min to raise the product temperature to 70° C., the heater power was switched off, and the warm water was allowed to naturally cool to 70° C. Using a programmed temperature controller, the product was gradually cooled from 70° C. to 35° C. at a decrease rate of 2° C./h. The time required for cooling to 35° C. was 20 hr.

COMPARATIVE EXAMPLE 4

GPC Analysis of dsRNA

The chain length of each sample obtained in Comparative Example 3 was measured by GPC analysis explained in Comparative Example 2. The results are collectively shown in Table 3.

Since the average chain length of the polyIC (400:400) subjected to the heating and cooling treatment under condition 1, 2 or 3 is extremely similar between #1 and #2, the data can be said to be reproducible distribution data of the chain length. While the ratio of the chain component showing long chain formation to not less than 2 kbp decreased more in conditions with milder temperature decrease, it was 13% even under condition 3 which was the mildest of those performed at this time. In all samples, the median value of the chain length exceeded the mean weight, which clarifies that the main chain length component constituting the sample is a chain length component longer than the mean weight. It is assumed that a chain component containing plural inosinic acid homopolymers and cytidylic acid homopolymers connected to each other constitutes the main part.

TABLE 3

| heating and cooling treatment | #1 chain length (bp) mean weight | #1 chain length (bp) median value | #1 >2 kbp ratio (wt %) | #2 chain length (bp) mean weight | #2 chain length (bp) median value | #2 >2 kbp ratio (wt %) |
|---|---|---|---|---|---|---|
| condition 1 | 498 | 728 | 33 | 489 | 728 | 34 |
| condition 2 | 442 | 672 | 23 | 439 | 672 | 23 |
| condition 3 | 401 | 622 | 13 | 406 | 622 | 13 |

COMPARATIVE EXAMPLE 5

Analysis of Changes in Chain Length of polyIC (400:400) by Re-Heating and Re-Cooling Changes in the chain length by a re-heating treatment were examined. In the same manner as in Comparative Example 2, polyIC (400:400) #1 and #2 were each dispensed by 1 ml to a plastic tube (inner volume 1.5 ml) with a screw cap, and a heating and cooling treatment was performed under condition 3, which was followed by the second heating and cooling treatment under condition 1 or condition 2. GPC analysis and chain length analysis of the samples after the heating and cooling treatments were performed. The results are collectively shown in Table 4.

The ratio of not less than 2 kbp that decreased to 13% by the heating and cooling treatment under condition 3 increased again to 32-33% or 18-21% by the re-treatment under condition 1 or condition 2. That is, it was clarified that even polyIC (400:400) after a treatment for suppressing production of the chain component to not less than 2 kbp shows a sharp increase in the ratio of the chain component to not less than 2 kbp when it is re-heated.

TABLE 4

| heating and cooling treatment | #1 chain length (bp) weight mean | #1 chain length (bp) median value | #1 >2 kbp ratio (wt %) | #2 chain length (bp) weight mean | #2 chain length (bp) median value | #2 >2 kbp ratio (wt %) |
|---|---|---|---|---|---|---|
| first time: condition 3 second time: not performed | 401 | 622 | 13 | 406 | 622 | 13 |
| first time: condition 3 second time: condition 1 | 466 | 672 | 33 | 470 | 672 | 32 |
| first time: condition 3 second time: condition 2 | 451 | 622 | 21 | 407 | 622 | 18 |

Examples of the present invention are shown below, to which the present invention is not limited.

EXAMPLE 1

Production of polyIC (25:400)

Inosinic acid homopolymer pI-25 (weight average chain length 29 bases, median value 29 bases) was dissolved in annealing buffer [composition: 100 mM HEPES buffer (pH 6.5), 100 mM NaCl] to produce a solution (10 ml) such that Abs 260 nm of 50-fold diluent was 1.0. Similarly, pC-400 (weight average chain length 344 bases, median value 324 bases) was dissolved in annealing buffer to produce a solution (10 ml) such that Abs 260 nm of 50-fold diluent was 1.0. To a 50 ml plastic tube were added pI-400 solution (5 ml) and pC-25 solution (5 ml), and two tubes containing the mixture was produced and stood at room temperature for 16 hr. 4M NaCl solution (0.5 ml) and isopropyl alcohol (10 ml) were added and mixed in each tube, polyIC was precipitated by centrifugation at 2800×g for 10 min, and the centrifugation supernatant was removed. 70% Ethanol (20 ml/tube) was added and mixed, polyIC was re-precipitated by centrifugation at 2800×g for 10 min, and the centrifugation supernatant was removed. 70% Ethanol (20 ml/tube) was added again and mixed, polyIC was re-precipitated by centrifugation at 2800×g for 10 min, and the centrifugation supernatant was removed. The tube was placed in a desiccator, and remaining ethanol was evaporated by drying under reduced pressure. Thereafter, annealing buffer was added at 10 ml/tube to produce polyIC (25:400) solutions #1 and #2 (#1 and #2 shows they were obtained by independent operation).

In the same manner as in Comparative Example 2, GPC analysis of polyIC (25:400) solution was performed and chain length analysis was performed.

Furthermore, using polyIC (25:400) solutions #1 and #2, samples that underwent a heating and cooling treatment under condition 1 and condition 2 were prepared by the same procedures as in Comparative Example 3, and GPC analysis and chain length analysis were performed. The analysis results are collectively shown in Table 5.

polyIC (25:400) did not show a long chain formation phenomenon of the chain length as observed with polyIC (400:400), and even when a heating and cooling treatment was applied, a phenomenon in which a chain component containing plural inosinic acid polymers and cytidylic acid polymers connected to each other becomes the main part was not observed.

TABLE 5

| heating and cooling treatment | #1 | | | #2 | | |
|---|---|---|---|---|---|---|
| | chain length (bp) | | >2 kbp | chain length (bp) | | >2 kbp |
| | mean weight | median value | ratio (wt %) | mean weight | median value | ratio (wt %) |
| untreated | 256 | 203 | 1 | 258 | 203 | 1 |
| condition 1 | 256 | 203 | 1 | 261 | 220 | 1 |
| condition 2 | 254 | 203 | 1 | 254 | 203 | 1 |

EXAMPLE 2

Production of polyIC (50:400)

In the same manner as described in Example 1 except that pI-25 was changed to inosinic acid homopolymer pI-50 (weight average chain length 41 bases, median value 35 bases), polyIC (50:400) solutions #1 and #2 were produced (#1 and #2 show they were obtained by independent operations). GPC analysis and chain length analysis of the polyIC (50:400) solutions were performed in the same manner as in Comparative Example 2. Furthermore, using polyIC (50:400) solutions #1 and #2, samples that underwent a heating and cooling treatment under condition 1 and condition 2 were prepared by the same procedures as in Comparative Example 3, and GPC analysis and chain length analysis were performed. The analysis results are collectively shown in Table 6.

polyIC (50:400) did not show a long chain formation phenomenon of the chain length as observed with polyIC (400:400), and even when a heating and cooling treatment was applied, a phenomenon in which a chain component containing plural inosinic acid polymers and cytidylic acid polymers connected to each other becomes the main part was not observed.

TABLE 6

| heating and cooling treatment | #1 | | | #2 | | |
|---|---|---|---|---|---|---|
| | chain length (bp) | | >2 kbp | chain length (bp) | | >2 kbp |
| | mean weight | median value | ratio (wt %) | mean weight | median value | ratio (wt %) |
| untreated | 288 | 239 | 1 | 288 | 239 | 1 |
| condition 1 | 278 | 220 | 1 | 275 | 220 | 1 |
| condition 2 | 268 | 203 | 1 | 268 | 203 | 1 |

EXAMPLE 3

Production of polyIC (100:400)

In the same manner as described in Example 1 except that pI-25 was changed to inosinic acid homopolymer pI-100 (weight average chain length 108 bases, median value 95 bases), polyIC (100:400) solutions #1 and #2 were produced (#1 and #2 show they were obtained by independent operations). Furthermore, using a part of polyIC (100:400) #1, a sample that underwent the heating and cooling treatment under condition 1 in Comparative Example 3 and a sample that underwent the heating and cooling treatment under condition 2 were prepared. Similarly, using polyIC (100:400) #2, samples that respectively underwent a heating and cooling treatment under condition 1 and condition 2 were prepared by the same procedures as in Comparative Example 3, and GPC analysis and chain length analysis of the respective samples were performed in the same manner as in Comparative Example 2. The analysis results are collectively shown in Table 7.

polyIC (100:400) did not show a long chain formation phenomenon of the chain length as observed with polyIC (400:400). The average chain length was somewhat different between #1 and #2 tubes, but the tubes after a heating and cooling treatment scarcely showed a difference. The ratio of the long chain component of not less than 2 kbp of the samples after the heating and cooling treatment was equivalent to that of the samples without the heating and cooling treatment, and even when a heating and cooling treatment was applied, a phenomenon in which a chain component containing plural inosinic chain polymers and cytidylic acid polymers connected to each other becomes the main part was not observed.

TABLE 7

| heating and cooling treatment | #1 | | | #2 | | |
|---|---|---|---|---|---|---|
| | chain length (bp) | | >2 kbp | chain length (bp) | | >2 kbp |
| | mean weight | median value | ratio (wt %) | mean weight | median value | ratio (wt %) |
| untreated | 302 | 349 | 3 | 339 | 404 | 4 |
| condition 1 | 303 | 187 | 4 | 315 | 203 | 4 |
| condition 2 | 249 | 173 | 2 | 272 | 187 | 2 |

PolyIC (100:400) #1 and PolyIC (100:400) 42 that underwent the heating and cooling treatment under condition 2 in the above were subjected again to the heating and cooling treatment under the above-mentioned condition 1, and the GPC analysis and chain length analysis were performed. The results are shown in Table 8.

PolyIC (100:400) did not show a long chain formation phenomenon of the chain length as observed with polyIC (400:400), and even when a re-heating and re-cooling treatment was applied, an increase in the long chain component was not observed.

TABLE 8

| heating and cooling treatment | #1 | | | #2 | | |
|---|---|---|---|---|---|---|
| | chain length (bp) | | >2 kbp | chain length (bp) | | >2 kbp |
| | mean weight | median value | ratio (wt %) | mean weight | median value | ratio (wt %) |
| first time: condition 2 second time: not performed | 249 | 173 | 2 | 272 | 187 | 2 |
| first time: condition 2 second time: condition 1 | 272 | 258 | 4 | 276 | 279 | 4 |

EXAMPLE 4

Production of polyIC (200:400)

In the same manner as described in Example 1 except that pI-25 was changed to inosinic acid homopolymer pI-200 (weight average chain length 188 bases, median value 157 bases), polyIC (200:400) solutions #1 and #2 were produced (#1 and #2 show they were obtained by independent operations). GPC analysis and chain length analysis of the polyIC (200:400) solutions were performed in the same manner as in Comparative Example 2. Furthermore, using polyIC (200:400) #1 and #2, samples that underwent a heating and cooling treatment under condition 1, condition 2 or condition 3 were prepared by the same procedures as in Comparative Example 3, and GPC analysis and chain length analysis were performed. The results are collectively shown in Table 9.

PolyIC (200:400) showed an increase in the long chain component of not less than 2 kbp up to 12-16%, but the long chain formation phenomenon decreased due to a heating and cooling treatment, and was almost completely suppressed by the heating and cooling treatment under condition 3 that provides most moderate cooling.

TABLE 9

| heating and cooling treatment | #1 chain length (bp) mean weight | #1 chain length (bp) median value | #1 >2 kbp ratio (wt %) | #2 chain length (bp) mean weight | #2 chain length (bp) median value | #2 >2 kbp ratio (wt %) |
|---|---|---|---|---|---|---|
| untreated | 377 | 537 | 12 | 413 | 537 | 16 |
| condition 1 | 379 | 500 | 10 | 389 | 500 | 11 |
| condition 2 | 313 | 301 | 5 | 327 | 325 | 6 |
| condition 3 | 244 | 134 | 1 | 298 | 146 | 3 |

Using the above-mentioned polyIC (200:400) #1 and #2 and in the same manner as in Comparative Example 3, samples that underwent the heating and cooling treatment under condition 3, followed by the second heating and cooling treatment under condition 1 or 2, were respectively prepared. GPC analysis and chain length analysis of the prepared samples were performed. The results are collectively shown in Table 10.

When polyIC (200:400) treated under condition 3 was re-heated and re-cooled under condition 1, the ratio of not less than 2 kbp increased to 9% and the chain component of not less than 2 kbp tended to increase somewhat. However, the ratio thereof was lower than the ratio of not less than 2 kbp (10-11%) (Table 9) obtained when polyIC (200:400) was subjected to the cooling and heat treatment under the same conditions. In the sample treated under condition 3 and re-treated under condition 2, the ratio of not less than 2 kbp was 4% and scarcely increased. That is, in polyIC (200:400), a severe increase in the long chain component of not less than 2 kbp due to the re-heating and re-cooling treatment observed in polyIC (400:400) was not observed.

TABLE 10

| heating and cooling treatment | #1 chain length (bp) mean weight | #1 chain length (bp) median value | #1 >2 kbp ratio (wt %) | #2 chain length (bp) mean weight | #2 chain length (bp) median value | #2 >2 kbp ratio (wt %) |
|---|---|---|---|---|---|---|
| first time: condition 3 second time: not performed | 244 | 134 | 1 | 298 | 146 | 3 |
| first time: condition 3 second time: condition 1 | 356 | 434 | 9 | 363 | 466 | 9 |
| first time: condition 3 second time: condition 2 | 309 | 123 | 4 | 317 | 123 | 4 |

EXPERIMENTAL EXAMPLE 2

Comparative Test of Recognition Property of Various polyICs by TLR-3 and RLR

Background

Animal cells are provided with three natural immune receptors that recognize dsRNA, which are Toll like receptor-3 (TLR-3) belonging to the TLR family, and Retinoic acid-inducible gene-I (RIG-I) and Melanoma differentiation-Associated protein 5 (MDA-5) belonging to the RLR family. TLR-3 is a receptor localized in the endosome of the cell. When dsRNA is bonded thereto, signal transduction via TRIF occurs and Type I interferon (IFN) and inflammatory cytokines are induced. The cells expressing TLR-3 are limited to particular immunocompetent cells such as myeloid dendritic cell, fibroblast and the like. On the other hand, RIG-I and MDA-5, which are generically referred to as RIG-I like receptor (RLR), are both localized in the cytoplasm of the cell, and have a dsRNA binding domain called CARD domain. When dsRNA is bonded to the CARD domain, signal transduction occurs via IPS1 in both RIG-I, MDA-5, and Type I IFN and inflammatory cytokines are induced. RLR is a receptor expressed in any cell including immunocompetent cells. RIG-I and MDA-5 show different recognition properties depending on the chain length of dsRNA and 5'-terminus structure.

The gene sequences and the primary structures of protein of TLR-3 and RLR have already been clarified. However, there is almost no finding permitting analogical inference of the secondary structure and primary structure of dsRNA that can be easily recognized by them. A single available report teaches that polyA:U is recognized by TLR-3 but is not easily recognized by RLR. There is no report on the inverse properties reported at this time; dsRNA that is recognized by RLR but not easily recognized by TLR-3.

The recognition property of TLR-3 and RLR can be evaluated using commercially available reporter cells. The TLR-3 recognition property can be evaluated using a cell obtained by incorporating TLR-3 gene and various NFκB inducible reporter genes into the genome of general cells such as 293 cell and the like and monitoring the level of activation of NFκB induced by TLR-3 stimulation. RLR recognition property can be evaluated using a cell obtained by incorporating TLR-3 gene and various NFκB and IRF3/7 inducible reporter genes into the genome of mouse fetal fibroblast that produces IFNβ in an RLR dependent manner, and monitoring the level of activation of NFκB and IRF3/7 induced by RLR stimulation.

We examined the TLR-3 recognition property and RLR recognition property of various polyICs, produced by annealing polyI having different chain lengths and about 400 nt polyC, by using a reporter cell. As a result, we have found a new fact that the RLR recognition property is constant irrespective of the chain length of polyI, but the recognition property of TLR-3 decreases more from the polyI chain length of about 100 nt as the length becomes shorter.

EXPERIMENTAL EXAMPLE 2.1

Comparison of RLR Recognition Property

The RLR recognition property of various dsRNAs was evaluated by comparison by using a reporter cell. RLR reporter cell C57/WT MEF (invivogen, USA) is a mouse primary fetal fibroblast strain introduced with a secretive placenta alkaliphosphatase (ALP) reporter gene induced by NF-κB and IRF3/7. Using this cell, the RLR recognition property of dsRNA can be relatively compared based on the induction amount of ALP. A reporter assay using the C57/WT MEF cell was performed according to the protocol of the maker. To be specific, C57/WT MEF was passage cultured in DMEM medium containing 10% bovine serum, the cell suspension thereof was seeded in a 12 well plate at 1 ml/well, and the cells were subjected to standing culture at 37° C., 5% $CO_2$ for about 20 hr. The medium was exchanged with bovine serum-free DMEM medium (1 ml/well), various dsRNAs (100 ng) or PBS was added together with transfection reagent LyoVec (invivogen, USA), and the cells were subjected to standing culture at 37° C., 5% $CO_2$. After 2 hr, bovine serum was added at 0.1 ml/well, the cells were further cultured for 22 hr, the culture supernatant was collected and the secreted ALP was quantitatively analyzed. For the quantitative analysis of ALP, QuantiBlue kit (invivogen, USA) was used, and the results were converted to numerical values with *E. coli*-derived ALP (Takara Bio Inc., Japan) as the standard product. The results thereof are collectively shown in Table 11. Since the ALP induction level does not change much depending on the dsRNA used, it was found that the RLR recognition property scarcely varies even when the chain length ratio of ssRNA constituting dsRNA is changed.

TABLE 11

| ssRNA species and weight average chain length | | ALP Found[1] | ALP induction level[2] | |
| --- | --- | --- | --- | --- |
| first chain | second chain | μU/ml | μU/ml | relative % |
| pI-400 (389b) | pC-400 (344b) | 64.4 | 43.5 | 100 |
| pI-200 (188b) | pC-400 (344b) | 65.7 | 44.8 | 103 |
| pI-100 (108b) | pC-400 (344b) | 59.7 | 38.8 | 89 |
| pI-50 (41b) | pC-400 (344b) | 56.8 | 35.9 | 83 |
| pI-25 (29b) | pC-400 (344b) | 61.8 | 40.9 | 94 |
| without addition of dsRNA (PBS was added) | | 20.9 | 0 | — |

[1]SEAP analytical value,
[2]amount of increase by dsRNA addition

EXPERIMENTAL EXAMPLE 2.2

Comparison of TLR-3 Binding Property

The TLR-3 recognition properties of various dsRNAs were compared by reporter cell assay. TLR-3 reporter cell HEK-Blue hTLR3 cell (invivogen, USA) is a recombinant HEK-293 cell obtained by incorporating NF-κB and AP-1 inducible ALP gene and human TLR-3 gene into the genome. Using this cell, the TLR-3 recognition property can be relatively compared based on the induction amount of ALP. A reporter assay using the HEK-Blue hTLR3 cell was performed according to the protocol of the maker. To be specific, HEK-Blue hTLR3 was passage cultured in DMEM medium containing 10% bovine serum supplemented with antibiotic Zeocin 100 mg/ml and antibiotic Blasticidin 10 mg/ml, the cell suspension thereof was seeded in a 12 well plate at 1 ml/well, and the cells were subjected to standing culture at 37° C., 5% $CO_2$ for about 44 hr. The medium was exchanged with bovine serum-free DMEM medium (1 ml) containing antibiotic Zeocin (100 mg/ml) and antibiotic Blasticidin (10 mg/ml), various dsRNAs (100 ng) or PBS was added, and the cells were subjected to standing culture at 37° C., 5% $CO_2$. After 2 hr from dsRNA addition, bovine serum was added at 0.1 ml/well, and 24 hr later, the culture supernatant was collected and induction level of ALP was compared. For the quantitative analysis of ALP, QuantiBlue kit (invivogen, USA) was used, and the results were converted to numerical values with *E. coli*-derived ALP (Takara Bio Inc., Japan) as the standard product. The results thereof are collectively shown in Table 12. As is clear from Table 12, when the chain length of polyI reached 108 nt or below, the ALP induction level decreased more as the chain length became shorter. That is, it was found that dsRNA showing completely new property that only the TLR-3 recognition property decreases while the RLR recognition property is maintained can be produced by setting the chain length of polyI to 108 nt or below.

TABLE 12

| ssRNA species and weight average chain length | | ALP Found[1] | ALP induction level[2] | |
| --- | --- | --- | --- | --- |
| first chain | second chain | μU/ml | μU/ml | relative % |
| pI-400 (389b) | pC-400 (344b) | 78.5 | 67.5 | 100 |
| pI-200 (188b) | pC-400 (344b) | 76.2 | 65.2 | 97 |
| pI-100 (108b) | pC-400 (344b) | 52.5 | 41.5 | 61 |
| pI-50 (41b) | pC-400 (344b) | 39.3 | 28.3 | 42 |
| pI-25 (29b) | pC-400 (344b) | 15.8 | 4.8 | 7 |
| without addition of dsRNA (PBS was added) | | 11.0 | 0 | — |

[1]SEAP analytical value,
[2]amount of increase by dsRNA addition

EXPERIMENTAL EXAMPLE 2.3

Experiment of TLR-3 Binding Property (Negative Control)

HEK-Blue Null1 cell (invivogen, USA) is a parent cell of HEM-Blue hTLR3 cell wherein only the human TLR-3 gene is not transfected, and corresponds to a negative control of this strain. In completely the same manner as in Experimental Example 2.2. except that HEK-Blue hTLR3 cell used in Experimental Example 2.2. was changed to HEM-Blue Null1 cell and antibiotic Blasticidin was not added to the medium, the test was performed to find that ALP was scarcely induced (Table 13). Therefore, it was confirmed that the ALP induction confirmed in Experimental Example 2.2. is a TLR-3 specific is signal transduction.

that IFNβ inducibility is maintained even when the chain length ratio of ssRNA constituting dsRNA is changed.

TABLE 13

| ssRNA species and weight average chain length | | ALP Found[1] | ALP induction level[2] |
|---|---|---|---|
| first chain | second chain | μU/ml | μU/ml |
| pC-400 (344b) | pI-400 (389b) | 6.6 | 0.7 |
| pI-200 (188b) | pC-400 (344b) | 6.8 | 0.9 |
| pI-100 (108b) | pC-400 (344b) | 6.9 | 1.0 |
| pI-50 (41b) | pC-400 (344b) | 6.2 | 0.3 |
| pI-25 (29b) | pC-400 (344b) | 5.8 | −0.1 |
| without addition of dsRNA (PBS was added) | | 5.9 | 0 |

[1]ALP analytical value,
[2]amount of increase by dsRNA addition

EXPERIMENTAL EXAMPLE 3

Evaluation of Natural Immunity Potentiation Activity and Toxicity of Various polyICs Background To confirm whether dsRNA wherein the chain length of the first chain constituting dsRNA is set to ½ or below to that of the second chain functions as a natural immunity potentiator, the strength of interferonβ inducibility was evaluated by comparison in a cellular experiment. Furthermore, to confirm whether the toxicity of the dsRNA decreases, single administration toxicity evaluation was performed using a mouse. As a result of these two evaluations, it could be confirmed that the toxicity is reduced while maintaining the natural immunity potentiation activity even when the chain length of the first chain constituting dsRNA is set to ½ or below to that of the second chain.

EXPERIMENTAL EXAMPLE 3.1

Evaluation of Natural Immunity Inducibility

To evaluate the strength of the natural immunity inducibility essential for functioning as an adjuvant, interferon (IFN)β inducibility of various dsRNAs was evaluated using human fetal fibroblast strain MRC-5 (Japanese Collection of Research Bioresources Cell Bank No. 9008) used for the study of natural immunity. To be specific, MRC-5 was passage cultured in MEM medium containing 10% bovine serum, the cell suspension thereof was seeded in a 12 well plate at 1 ml/well, and the cells were subjected to standing culture at 37° C., 5% $CO_2$ for about 20 hr. The medium was exchanged with bovine serum-free MEM medium (1 ml/well), various dsRNAs (30 μg) or PBS was added together with transfection reagent LyoVec (invivogen, USA), and the cells were subjected to standing culture at 37° C., 5% $CO_2$. After 2 hr, bovine serum was added at 0.1 ml/well, and the cells were further cultured for 22 hr. The culture supernatant was collected at 10 h, 24 h after dsRNA addition and IFNβ contained in the culture supernatant was quantitatively analyzed. For the quantitative analysis of IFNβ, IFNβ ELISA kit (KAMAKURA TECHNO-SIENCE, INC., Japan) was used. The results thereof are collectively shown in Table 14. Since the IFNβ induction level does not change much depending on the dsRNA used, it was clarified

TABLE 14

| ssRNA species and weight average chain length | | IFNβ (IU/ml) | |
|---|---|---|---|
| first chain | second chain | 10 h later | 24 h later |
| pI-400 (388b) | pC-400 (406b) | 25 | 140 |
| pI-200 (205b) | pC-400 (404b) | 29 | 170 |
| pI-100 (96b) | pC-400 (402b) | 37 | 153 |
| pI-50 (51b) | pC-400 (405b) | 39 | 197 |
| without addition of dsRNA (PBS was added) | | 0 | 0 |

EXPERIMENTAL EXAMPLE 3.2

Evaluation of Toxicity

PolyI:C produced using polyI and polyC having various chain lengths was dissolved in saline to prepare solutions having a concentration of 5 mg/ml to 20 mg/ml. These aqueous solutions were intraperitoneally administered once to healthy male Crlj:CD1 mice (6-week-old), and acute toxicity was compared. Mice were housed in a mouse cage (5 per cage) placed under the environment of room temperature 22° C.±3° C., humidity 55%110%, ventilation frequency 10 times or more/h, illumination 12 hr/day, and bred under the condition permitting free ingestion of water and feed. About 1 week of acclimation period was set before intraperitoneal administration and, after administration, the mice were bred for 7 days counting the day of administration as day 1, and monitored. Table 15 collectively shows the dose of polyI:C and survival number after breeding for 7 days. The number of mice survived was improved by setting the chain length of the first chain to ½ or below to that of the second chain. That is, decrease in the toxicity was confirmed.

TABLE 15

| ssRNA species and weight average chain length | | number of mice survived/administration number polyI:C dose (mg/kg/day) | | |
|---|---|---|---|---|
| first chain | second chain | 100 | 200 | 400 |
| pI-400 (388b) | pC-400 (406b) | 2/5 | 0/5 | — |
| pI-200 (205b) | pC-400 (404b) | 5/5 | 2/5 | 0/5 |
| pI-100 (96b) | pC-400 (402b) | 5/5 | 3/5 | 0/5 |
| pI-50 (51b) | pC-400 (405b) | 5/5 | 5/5 | 4/5 |

This application is based on patent application No. 2012-267012 filed in Japan (filing date: Dec. 6, 2012) and patent application No. 2013-145471 filed in Japan (filing date: Jul. 11, 2013), the contents of which are incorporated in full herein.

The invention claimed is:

1. A method of producing double-stranded ribonucleic acid (dsRNA) having a weight average chain length within the range of 0.1 kilobase pairs (kbp) to 2.0 kbp, or a salt thereof, comprising (1) a step of preparing a single-stranded RNA (ssRNA) consisting of the same type of ribonucleotide,
(2) a step of preparing an ssRNA having a base sequence having complementarity of a level capable of forming a double strand to said (1) ssRNA, and
(3) a step of annealing said (1) ssRNA and said (2) ssRNA,
wherein the weight average chain length of ssRNA in said (1) is not more than ½ to that of said (2) and is 0.02-0.05 kilobase (kb), and the weight average chain length of ssRNA of said (2) is 0.2-1.0 kb.

2. The method according to claim 1, wherein ssRNA of said (1) is a polyinosinic acid, and ssRNA of said (2) is ssRNA containing cytidylic acid at a ratio of not less than 80%.

* * * * *